(12) United States Patent
Henley et al.

(10) Patent No.: US 9,849,242 B2
(45) Date of Patent: Dec. 26, 2017

(54) AUTOINJECTOR

(71) Applicant: SANOFI-AVENTIS DEUTSCHLAND GMBH, Frankfurt am Main (DE)

(72) Inventors: Thomas Henley, Biggleswade (GB); David Cross, Hertfordshire (GB); Douglas Ivan Jennings, Herts (GB); Ryan Anthony McGinley, Cambridge (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 692 days.

(21) Appl. No.: 14/360,492

(22) PCT Filed: Nov. 23, 2012

(86) PCT No.: PCT/EP2012/073467
§ 371 (c)(1),
(2) Date: May 23, 2014

(87) PCT Pub. No.: WO2013/076246
PCT Pub. Date: May 30, 2013

(65) Prior Publication Data
US 2014/0343505 A1    Nov. 20, 2014

(30) Foreign Application Priority Data
Nov. 24, 2011   (EP) ..................... 11190587

(51) Int. Cl.
*A61M 5/20*   (2006.01)
*A61M 5/32*   (2006.01)
*A61M 5/24*   (2006.01)

(52) U.S. Cl.
CPC ........ *A61M 5/2033* (2013.01); *A61M 5/3234* (2013.01); *A61M 5/3204* (2013.01);
(Continued)

(58) Field of Classification Search
CPC .............. A61M 5/2033; A61M 5/3234; A61M 5/3204; A61M 5/326; A61M 2005/202;
(Continued)

(56) References Cited

U.S. PATENT DOCUMENTS 6,270,479 B1 *  8/2001  Bergens .............. A61M 5/2033
                                                    604/156
2009/0312705 A1 * 12/2009 Grunhut .............. A61M 5/2033
                                                    604/110

FOREIGN PATENT DOCUMENTS

CN        1845765      10/2006
EP        2364741 A1    9/2011
(Continued)

*Primary Examiner* — Emily Schmidt
*Assistant Examiner* — Lauren M Peng
(74) *Attorney, Agent, or Firm* — Fish & Richardson P.C.

(57) ABSTRACT

Described is an autoinjector comprising a front case having a first rib and a second rib, and a rear case telescopically coupled to the front case and having latch arms adapted to engage the first rib and the second rib. When the front case is in a first position relative to rear case, the latch arms are engaged to the first rib. When the latch arms disengage the first rib, the front case translates to a second position relative to the rear case, an axial distance between the front case and the rear case increases relative to the first position, the latch arms engage the second rib.

24 Claims, 12 Drawing Sheets

(52) U.S. Cl.
CPC ....... *A61M 5/326* (2013.01); *A61M 2005/202* (2013.01); *A61M 2005/206* (2013.01); *A61M 2005/208* (2013.01); *A61M 2005/2407* (2013.01); *A61M 2005/2492* (2013.01); *A61M 2005/3231* (2013.01); *A61M 2205/582* (2013.01); *A61M 2205/584* (2013.01)

(58) Field of Classification Search
CPC ...... A61M 2005/206; A61M 2005/208; A61M 2005/2492; A61M 2005/3231; A61M 2205/582; A61M 2205/584
See application file for complete search history.

(56) References Cited

FOREIGN PATENT DOCUMENTS

| | | |
|---|---|---|
| WO | 9748430 A1 | 12/1997 |
| WO | 9903529 A2 | 1/1999 |
| WO | 2005021071 A1 | 3/2005 |
| WO | 2011075760 A1 | 6/2011 |

\* cited by examiner

AUTOINJECTOR

CROSS REFERENCE TO RELATED APPLICATIONS

The present application is a U.S. National Phase Application pursuant to 35 U.S.C. §371 of International Application No. PCT/EP2012/073467 filed Nov. 23, 2012, which claims priority to European Patent Application No. 1 filed Nov. 24, 2011. The entire disclosure contents of these applications are herewith incorporated by reference into the present application.

FIELD OF INVENTION

The invention relates to an autoinjector for administering a medicament.

BACKGROUND

Administering an injection is a process which presents a number of risks and challenges for users and healthcare professionals, both mental and physical Injection devices typically fall into two categories—manual devices and autoinjectors. In a conventional manual device, a user must provide force to drive a medicament through a needle. This is typically done by some form of button/plunger that has to be continuously pressed during the injection. There are numerous disadvantages for the user from this approach. For example, if the user stops pressing the button/plunger, the injection will stop and may not deliver an intended dose to a patient. Further, the force required to push the button/plunger may be too high for the user (e.g., if the user is elderly). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to the present invention comprises a front case having a first rib and a second rib, and a rear case telescopically coupled to the front case and having latch arms adapted to engage the first rib and the second rib. When the front case is in a first position relative to rear case, the latch arms are engaged to the first rib. When the latch arms disengage the first rib, the front case translates to a second position relative to the rear case, an axial distance between the front case and the rear case increases relative to the first position, the latch arms engage the second rib.

In an exemplary embodiment, the autoinjector further comprises an interlock sleeve slidably disposed in the front case, and a sleeve spring adapted to apply a biasing force to the interlock sleeve relative to the front case.

In an exemplary embodiment, the autoinjector further comprises a syringe carrier slidably disposed in the front case, and a carrier spring adapted to apply a biasing force to the syringe carrier relative to the front case.

In an exemplary embodiment, the autoinjector further comprises a latch sleeve slidably disposed in the front case, and a latch sleeve spring adapted to apply a biasing force to the latch sleeve relative to the front case. The latch sleeve prevents disengagement of the latch arms and the first rib until the latch sleeve is displaced against the biasing force of the latch sleeve spring.

In an exemplary embodiment, the autoinjector further comprises a drive carriage disposed in the rear case, and a drive spring adapted to apply a force to the drive carriage relative to the rear case.

In an exemplary embodiment, the autoinjector further comprises a trigger button disposed on the rear case.

In an exemplary embodiment, the autoinjector further comprises a first latch mechanism adapted to prevent movement of the syringe carrier in a distal direction relative to the front case. The first latch mechanism includes a syringe backward latch pivotable between a first angular position in which the latch engages the syringe carrier and a second angular position in which the latch disengages the syringe carrier. The interlock sleeve includes a first arm adapted to engage the backward latch and move the backward latch from the first angular position to the second angular position when the interlock sleeve moves relative to the front case.

In an exemplary embodiment, the autoinjector further comprises a second latch mechanism adapted to prevent movement of the syringe carrier in a proximal direction relative to the front case. The second latch mechanism includes a resilient syringe forward latch adapted to deflect when the syringe carrier moves in a distal direction relative to the front case and return to a non-deflected position to abut the syringe carrier when the syringe carrier moves in the proximal direction relative to the front case. The second latch mechanism includes a lever coupled to the forward latch, actuation of the lever causes the forward latch to disengage the syringe carrier.

In an exemplary embodiment, the autoinjector further comprises a third latch mechanism adapted to prevent actuation of the trigger button. The third latch mechanism includes a lockout bar slidably disposed in the rear case and having a recess. The lockout bar abuts the trigger button to prevent movement of the trigger button until a second arm on the interlock sleeve pushes the lockout bar in the proximal direction to align the recess with the trigger button.

In an exemplary embodiment, the autoinjector further comprises a slider movably arranged on the rear case. The slider includes an internal boss adapted to engage the drive carriage.

In an exemplary embodiment, the interlock sleeve abuts the latch arms in the first position to prevent the latch arms from disengaging the first rib. The latch sleeve abuts the interlock sleeve in the first position to prevent the latch arms from disengaging the first rib.

In an exemplary embodiment, the autoinjector further comprises a cap having resilient barbs adapted to engage a needle sheath. The barbs are maintained in engagement with the needle sheath by the interlock sleeve.

In an exemplary embodiment, the autoinjector further comprises a syringe having a needle retraction mechanism. Actuation of the needle retraction mechanism causes the front case to move from the first position to the second position. When the needle retraction mechanism applies a force to the drive carriage, a remaining force in the drive spring prevents movement of the drive carriage relative to the rear case and causes axial movement of the front case relative to the rear case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
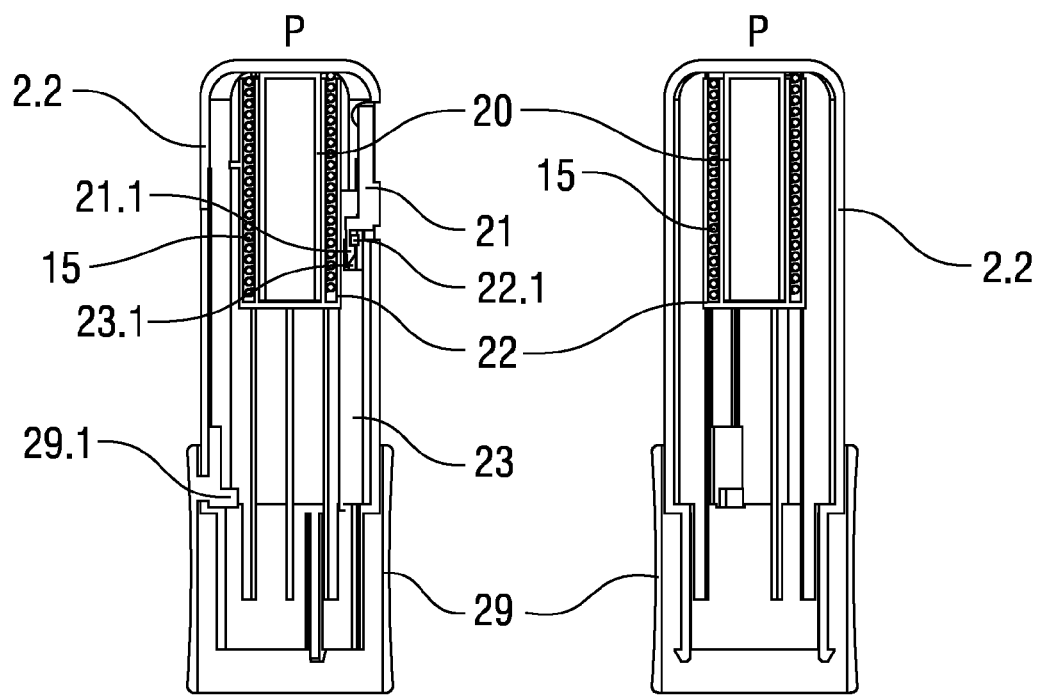
FIG. 1 shows two longitudinal sections of an exemplary embodiment of an autoinjector according to the present invention.
Figure 1B:
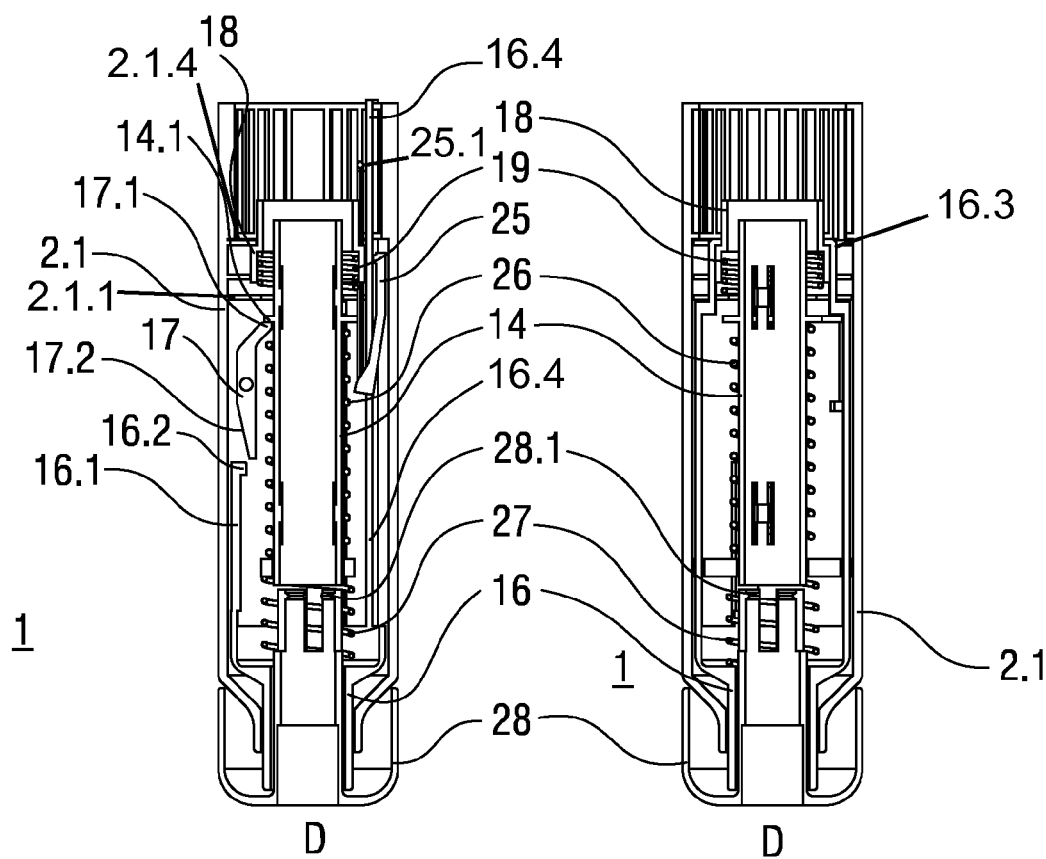

FIGS. 1A and 1B show longitudinal sections of an exemplary embodiment of an autoinjector 1 in different section planes. The autoinjector 1 comprises an elongate housing having a front case 2.1 and a rear case 2.2 which may be separated. While the exemplary embodiment shown in FIGS. 1A and 1B shows the front and rear cases 2.1, 2.2 as being completely separable, in other exemplary embodiments, the cases 2.1, 2.2 may be hingedly coupled together. In another exemplary embodiment, the cases 2.1, 2.2 may be separable along a longitudinal axis of the housing, as opposed to a transverse axis of the housing.

In an exemplary embodiment, the front case 2.1 includes a carrier 14 adapted to hold a syringe. The carrier 14 is axially movable relative to the front case 2.1 and is biased toward a proximal direction P by a carrier spring 26 which bears proximally against a shoulder 14.1 on the carrier 14 and distally against a ledge formed in a distal portion of the front case 2.1.

The front case 2.1 also includes an interlock sleeve 16. The interlock sleeve 16 is axially movable relative to the front case 2.1 and is biased toward a distal direction D by a sleeve spring 27 which bears proximally against the ledge in the distal portion of the front case 2.1 and distally against the interlock sleeve 16. The interlock sleeve 16 is adapted to project distally through a distal opening in the front case 2.1, such that the interlock sleeve 16 contacts an injection site during an injection procedure, as explained further below.

The front case 2.1 also includes a latch sleeve 18 adapted to ensure that the front case 2.1 and the rear case 2.2 remain engaged during an injection procedure, as described further below. The latch sleeve 18 is axially movable relative to the front case 2.1 and is biased toward the proximal direction P by a latch sleeve spring 19 which bears proximally against the latch sleeve 18 and distally against a third rib 2.1.1 formed in a proximal portion of the front case 2.1. Hooks 16.3 on a proximal end of the interlock sleeve 16 are adapted to engage a shoulder formed on the latch sleeve 18. The hooks 16.3 limit extension of the interlock sleeve 16 relative to the front case 2.1, because the latch sleeve spring 19 requires more force to compress it than the sleeve spring 27. Further, a fourth rib 2.1.4 formed on the first case 2.1 abuts the latch sleeve 18 and prevents the latch sleeve 18 from moving proximally relative to the front case 2.1.

In an exemplary embodiment, the autoinjector 1 includes one or more latch mechanisms for preventing inadvertent actuation of the autoinjector 1. A first latch mechanism is adapted to prevent movement of the carrier 14 relative to the front case 2.1 prior to retraction of the interlock sleeve 16. In an exemplary embodiment, the first latch mechanism comprises a syringe backwards latch 17 pivotably coupled to a peg on the front case 2.1. A proximal nose 17.1 of the syringe backwards latch 17 is adapted to engage the shoulder 14.1 on the carrier 14. A distal ramp 17.2 of the syringe backwards latch 17 is adapted to engage a first arm 16.1 extending proximally from the interlock sleeve 16. A proximal end of the first arm 16.1 may include a protrusion 16.2 adapted to engage the distal ramp 17.2. As explained further below, when the interlock sleeve 16 is retracted in the proximal direction P relative to the front case 2.1, the first arm 16.1 engages the distal ramp 17.2, the syringe backwards latch 17 pivots and the proximal nose 17.1 disengages the shoulder 14.1, allowing the carrier 14 to move axially in the distal direction D relative to the front case 2.1. In an exemplary embodiment, a latch spring (not shown) may bias the syringe backwards latch 17 in an angular position in which the nose 17.1 engages the shoulder 14.1.

In another exemplary embodiment the syringe backwards latch 17 may have a straight end instead of the ramp 17.2 in which case a ramp may be provided at the protrusion 16.2. In yet another exemplary embodiment both the syringe backwards latch 17 and the protrusion 16.2 may have corresponding ramped surfaces.

In an exemplary embodiment, the front case 2.1 includes a second latch mechanism for preventing movement of the carrier 14 in the proximal direction P after the injection procedure. The second latch mechanism may include a resilient syringe forward latch 25 which deflects when it is engaged by the shoulder 14.1 as the carrier 14 moves axially in the distal direction D. When, under force of the carrier spring 26, the carrier 14 moves in the proximal direction P, the shoulder 14.1 abuts the syringe forward latch 25 which has returned to its non-deflected position. The latch 25 may include a lever 25.1 which can be pressed manually to re-deflect the syringe forward latch 25 when resetting the autoinjector 1, as explained further below.

In an exemplary embodiment, the rear case 2.2 comprises a drive spring 15 adapted to apply a force to a plunger on a syringe in the autoinjector 1. The drive spring 15 is arranged on a fixed sleeve 20 which is coupled to a proximal end of the rear case 2.2. The drive spring 15 bears proximally on the rear case 2.2 and distally on a drive carriage 22 which is arranged telescopically on the fixed sleeve 20. The drive carriage 22 is adapted to move axially relative to the rear case 2.2 and is adapted to engage a plunger on a syringe.

In an exemplary embodiment, a trigger button 21 is arranged on the rear case 2.2. The trigger button 21 may be disposed on a lateral surface of the rear case 2.2 or a proximal end of the rear case 2.2. The trigger button 21 may include a catch arm 21.1 adapted to engage a catch 22.1 on the drive carriage 22, preventing axial movement of the drive carriage 22 in the distal direction D. When the trigger button 21 is pressed, the catch arm 21.1 disengages the catch 22.1, allowing the drive carriage 22 to be propelled in the distal direction D by the force of the drive spring 15.

In an exemplary embodiment, the rear case 2.2 includes a third latch mechanism for preventing inadvertent actuation of the autoinjector 1. The third latch mechanism is adapted to prevent movement of the trigger button 21 prior to retraction of the interlock sleeve 16 into the front case 2.1. In an exemplary embodiment, the third latch mechanism comprises a trigger lockout bar 23 axially movable relative to the rear case 2.2, operably coupled to the interlock sleeve 16, and adapted to engage the trigger button 21. The trigger lockout bar 23 may be biased (e.g., by a spring, not shown) in a position abutting and preventing movement of the trigger button 21 relative to the rear case 2.2. Retraction of the interlock sleeve 16 relative to the front case 2.1 may displace the trigger lockout bar 23 in the proximal direction P, and align a recess 23.1 on the trigger lockout bar 23 with the trigger button 21. The trigger button 21 can then be pressed and received by the recess 23.1.

In an exemplary embodiment, a second arm 16.4 extending proximally from the interlock sleeve 16 may engage the trigger lockout bar 23 when the front case 2.1 is coupled to the rear case 2.2. When the interlock sleeve 16 is retracted into the front case 2.1, the second arm 16.4 may push the trigger lockout bar 23 in the proximal direction P relative to the rear case 2.2 to align the recess 23.1 with the trigger button 21.

Figures 2A, 2B:
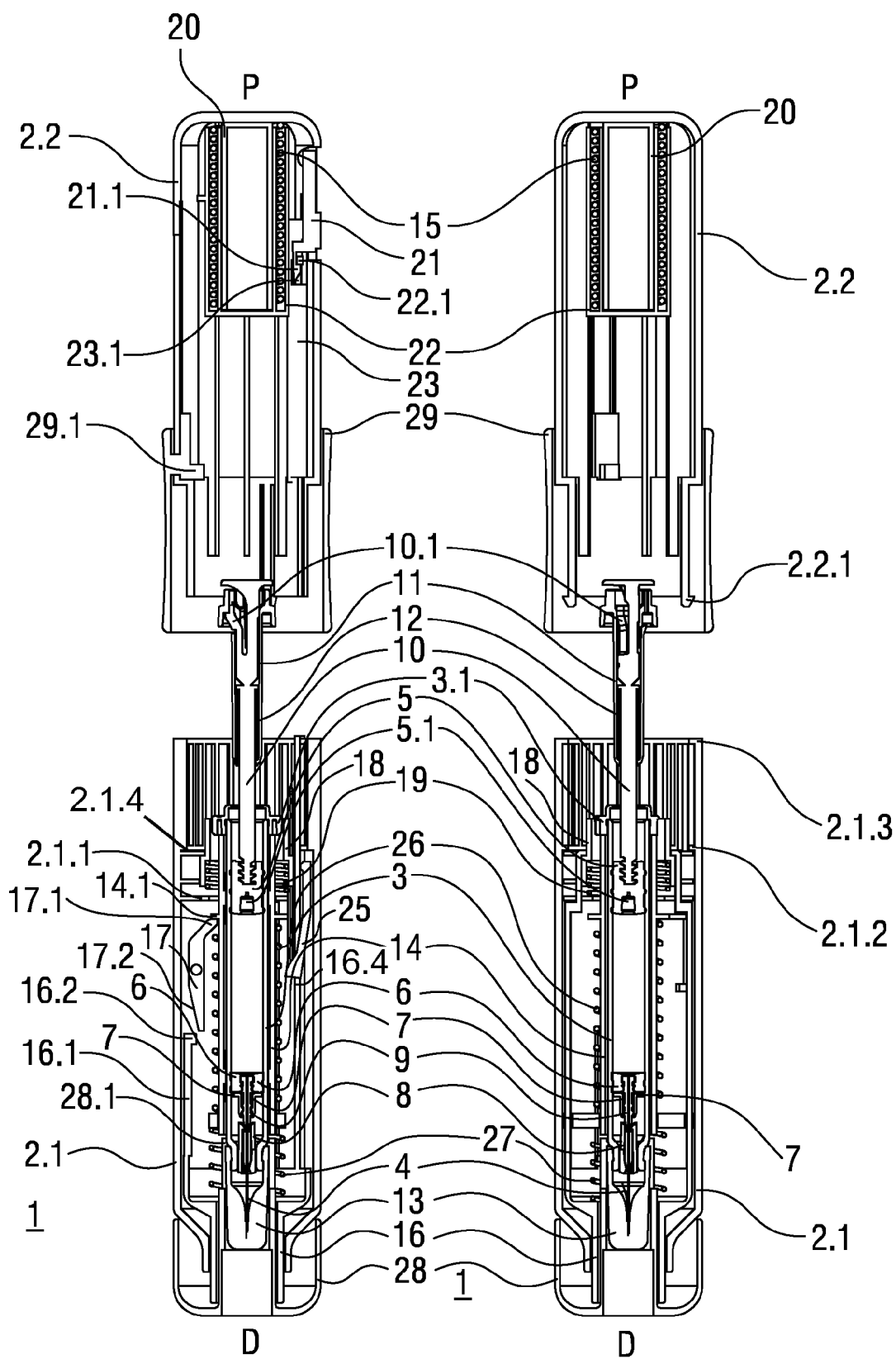
FIG. 2 shows an exemplary embodiment of an autoinjector during insertion of a syringe.

In an exemplary embodiment as shown in FIGS. 2A and 2B, the autoinjector 1 includes a locking mechanism for locking the front case 2.1 and the rear case 2.2 in a coaxial position. In an exemplary embodiment, the locking mechanism comprises two resilient latch arms 2.2.1 extending distally from the rear case 2.2 and adapted to selectively engage a first rib 2.1.2 and a second rib 2.1.3 (proximal of the first rib 2.1.2) in the front case 2.1, as explained further below.

Referring back to FIGS. 1A and 1B, the locking mechanism may further include a slider 29 movably mounted on the rear case 2.2. The slider 29 may be spring-loaded and biased in the distal direction D (or a lock position). An internal boss 29.1 on the slider 29 may be adapted to engage the drive carriage 22 when the slider 29 is moved from the lock position proximally to an unlock position. Movement of the slider 29 and the drive carriage 22 in the proximal direction may re-compress the drive spring 15 for subsequent use.

A protective cap 28 may be attached to a distal end of the front case 2.1. The cap 28 may include resilient barbs 28.1 (shown in FIGS. 2A and 2B) adapted to engage a needle sheath on a needle of a syringe in the autoinjector 1.

In FIGS. 1A and 1B the front case 2.1 and rear case 2.2 are separate, and a syringe has not yet been inserted.

FIGS. 2A and 2B show the front case 2.1 and rear case 2.2 still separate but with a syringe 3 inserted into the carrier 14. The syringe 3 may be inserted into the carrier 14 until a finger flange 3.1 on the syringe 3 abuts a proximal end of the carrier 14.

In an exemplary embodiment, the syringe 3 may have a needle retraction mechanism. For example, the syringe 3 may be a Unifill or Unitract syringe from Unilife Corporation. The syringe 3 may include a barrel, a stopper 5 slidably arranged within the barrel, and a needle 4 arranged on a distal end of the syringe 3. The syringe 3 may include a needle retraction mechanism comprising a needle seal 6 slidably arranged in a distal end of the barrel, an ejector ring 7 distal of the needle seal 6, a needle retainer 8 arranged on the distal end of the syringe 3 and adapted to engage a needle mount 9 coupled to the needle 4. The stopper 5 includes a cavity 5.1 adapted to engage the needle mount 9, as described in more detail below.

In the exemplary embodiment, the syringe 3 includes an inner plunger 10 telescopically arranged on an outer plunger 11. A distal end of the inner plunger 10 is coupled to the stopper 5. A plunger spring 12 biases the outer plunger 11 relative to the inner plunger 10. A resilient arm 10.1 on the inner plunger 10 engages the inner plunger 10 to the outer plunger 11. A release ring 3.2 on the finger flange 3.1 of the syringe 3 is adapted to engage the resilient arm 10.1, causing the arm 10.1 to deflect and disengage the outer plunger 11. When the arm 10.1 disengages the outer plunger 11, the plunger spring 12 expands, and the inner plunger 10 can move axially relative to the outer plunger 10. The outer plunger 11 comprises non return features (not illustrated) for engaging it to the release ring 3.2.

When the syringe 3 is assembled, a needle sheath 13 is attached to the needle 4.

Figures 3A, 3B:
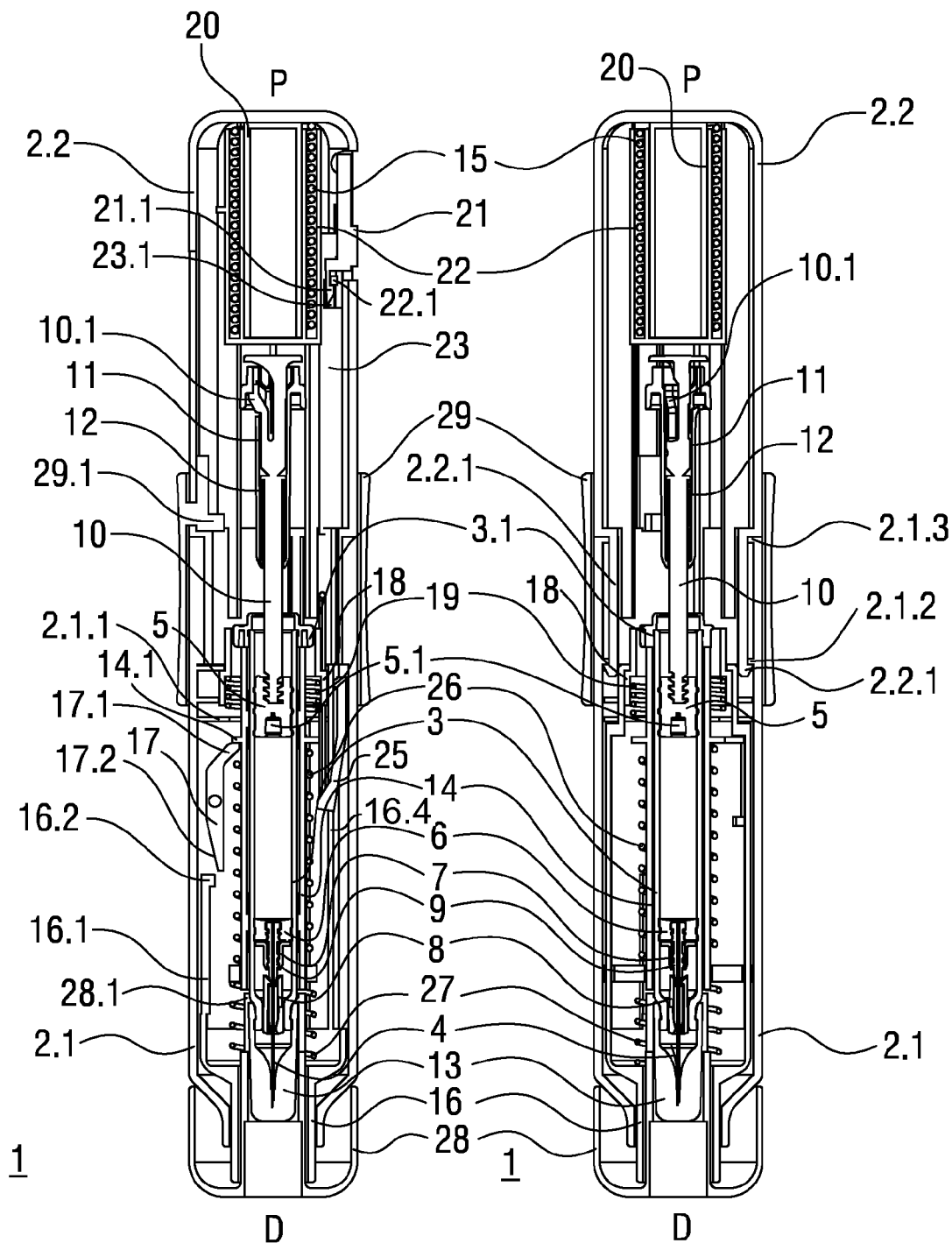
FIG. 3 shows an exemplary embodiment of an autoinjector when assembled.

As shown in FIGS. 3A and 3B, once the syringe 3 is placed in the carrier 14, the front case 2.1 may be coupled to the rear case 2.2 when the latch arms 2.2.1 on the rear case 2.2 engage the first rib 2.1.2 in the front case 2.1. In an exemplary embodiment, a feedback (e.g., an audible click) may be provided when the latch arms 2.2.1 engage the first rib 2.1.2 to notify the user that the front case 2.1 is secured to the rear case 2.2. The latch arms 2.2.1 and the first rib 2.1.2 may have corresponding ramped surfaces to facilitated engagement/disengagement. As shown in FIG. 3B, the latch arms 2.2.1 are maintained in engagement with the first rib 2.1.2, because the latch arms 2.2.1 abut the hooks 16.3 and the hooks 16.3 abut the latch sleeve 18. The slider 29 may be in an extended position, covering a joint between the front and rear cases 2.1, 2.2.

Figures 4A, 4B:
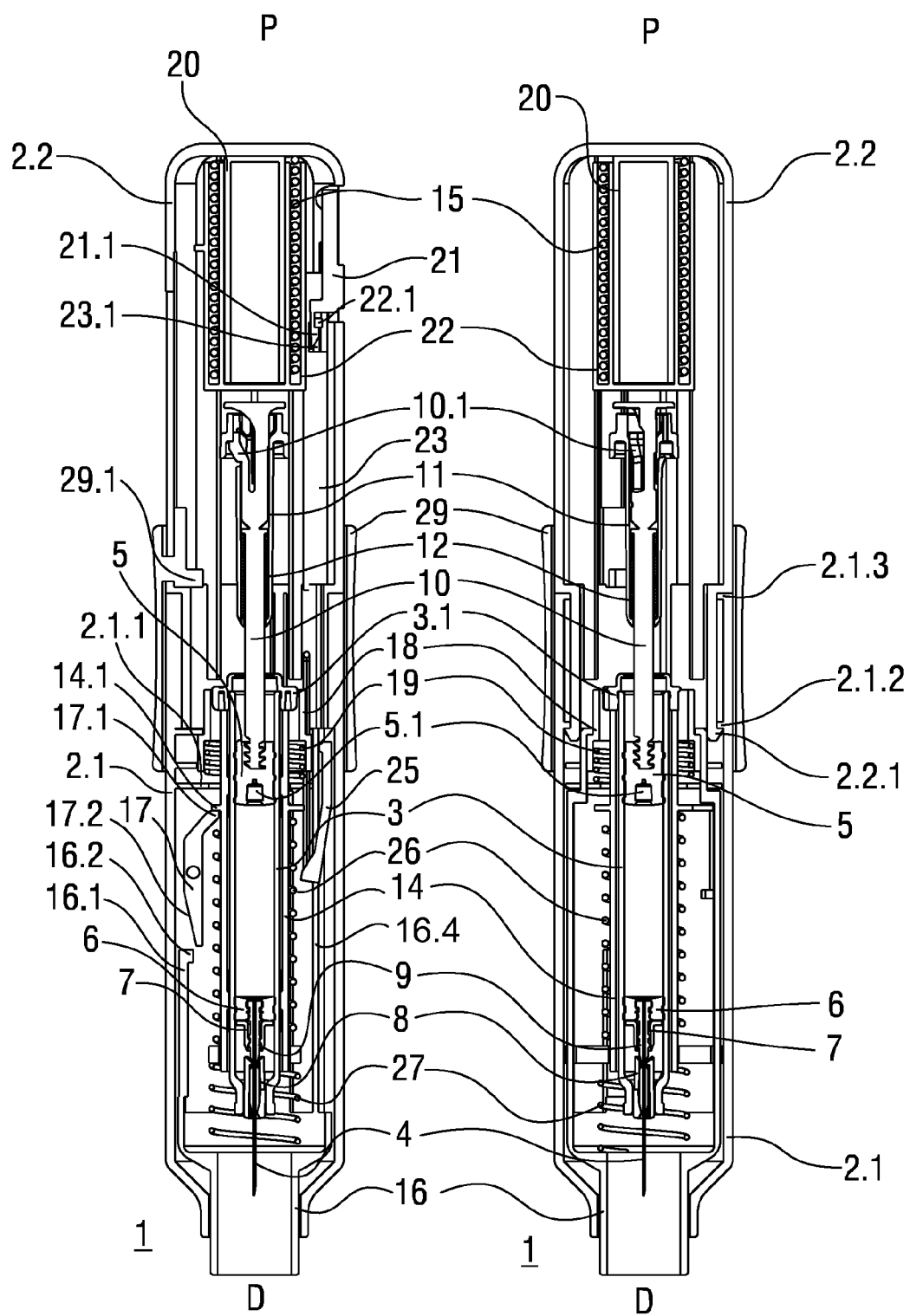
FIG. 4 shows an exemplary embodiment of an autoinjector after removal of a cap.

In FIGS. 4A and 4B, the cap 28 has been removed from the autoinjector 1. When the cap 28 is removed (e.g., by pulling in the distal direction D), the barbs 28.1 on the cap 28 engage the needle sheath 13 and remove the needle sheath 13 with the cap 28. Once the cap 28 is removed, the barbs 28.1 are no longer constrained so the protective needle sheath 13 is released and may be easily removed from the cap 28. For example, the barbs 28.1 may be biased radially away from the longitudinal axis of the autoinjector 1. When coupled to the autoinjector 1, the barbs 28.1 may be deflected and constrained by the distal end of the interlock sleeve 16. Thus, when the cap 28 is separated from the autoinjector 1, the barbs 28.1 may return to their non-deflected position and release the needle sheath 13.

When the cap 28 is removed from the autoinjector 1, the interlock sleeve 16 is in an extended position, protruding from the distal opening of the front case 2.1.

Figures 5A, 5B:
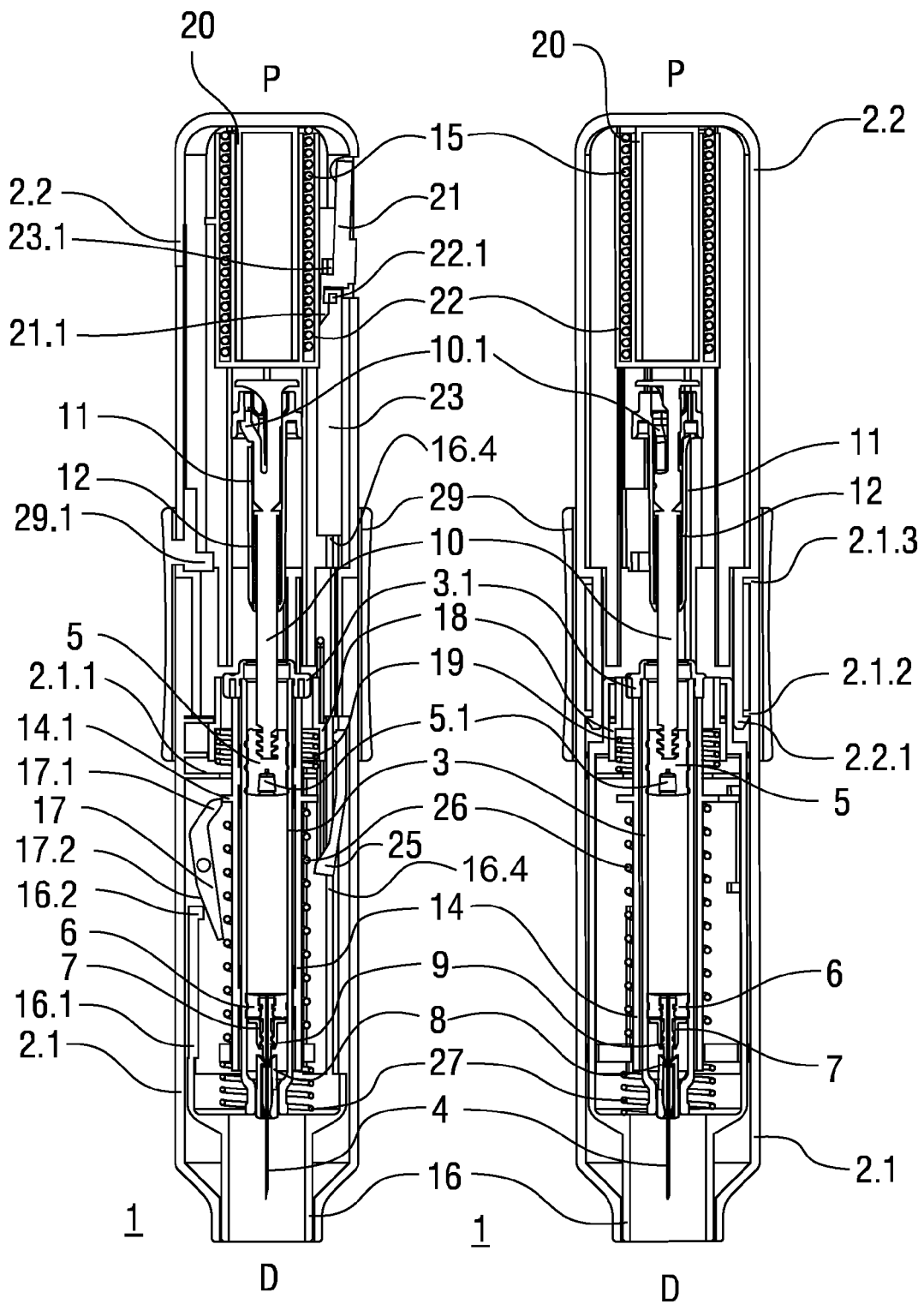
FIG. 5 shows an exemplary embodiment of an autoinjector pressed against an injection site.

In FIGS. 5A and 5B, the interlock sleeve 16 is in a retracted position relative to the front case 2.1, because the autoinjector 1 has been pressed against an injection site. As the interlock sleeve 16 translates in the proximal direction P relative to the front case 2.1, the first arm 16.1 engages the distal ramp 17.2 of the syringe backward latch 17, causing the syringe backward latch 17 to rotate and the nose 17.1 to disengage the shoulder 14.1 on the carrier 14.

Also, the second arm 16.4 engages the trigger lockout bar 23 and pushes the trigger lockout bar 23 in the proximal direction P relative to the rear case 2.2. When the trigger lockout bar 23 moves proximally relative to the rear case 2.2, the recess 23.1 is aligned with the trigger button 21. The autoinjector 1 can now be activated by pressing the trigger button 21.

Translation of the interlock sleeve 16 in the proximal direction P also moves the proximal end of the interlock sleeve 16 behind the latch arms 2.2.1 on the rear case 2.2, which further reinforces the engagement of the latch arms 2.2.1 and the first rib 2.1.2 on the front case 2.1. The hooks 16.3 on the interlock sleeve 16 disengage the shoulder on the latch sleeve 18. However the latch sleeve 18 remains in position relative to the front case 2.1, because the shoulder on the latch sleeve 18 abuts the fourth rib 2.1.4.

Figures 6A, 6B:
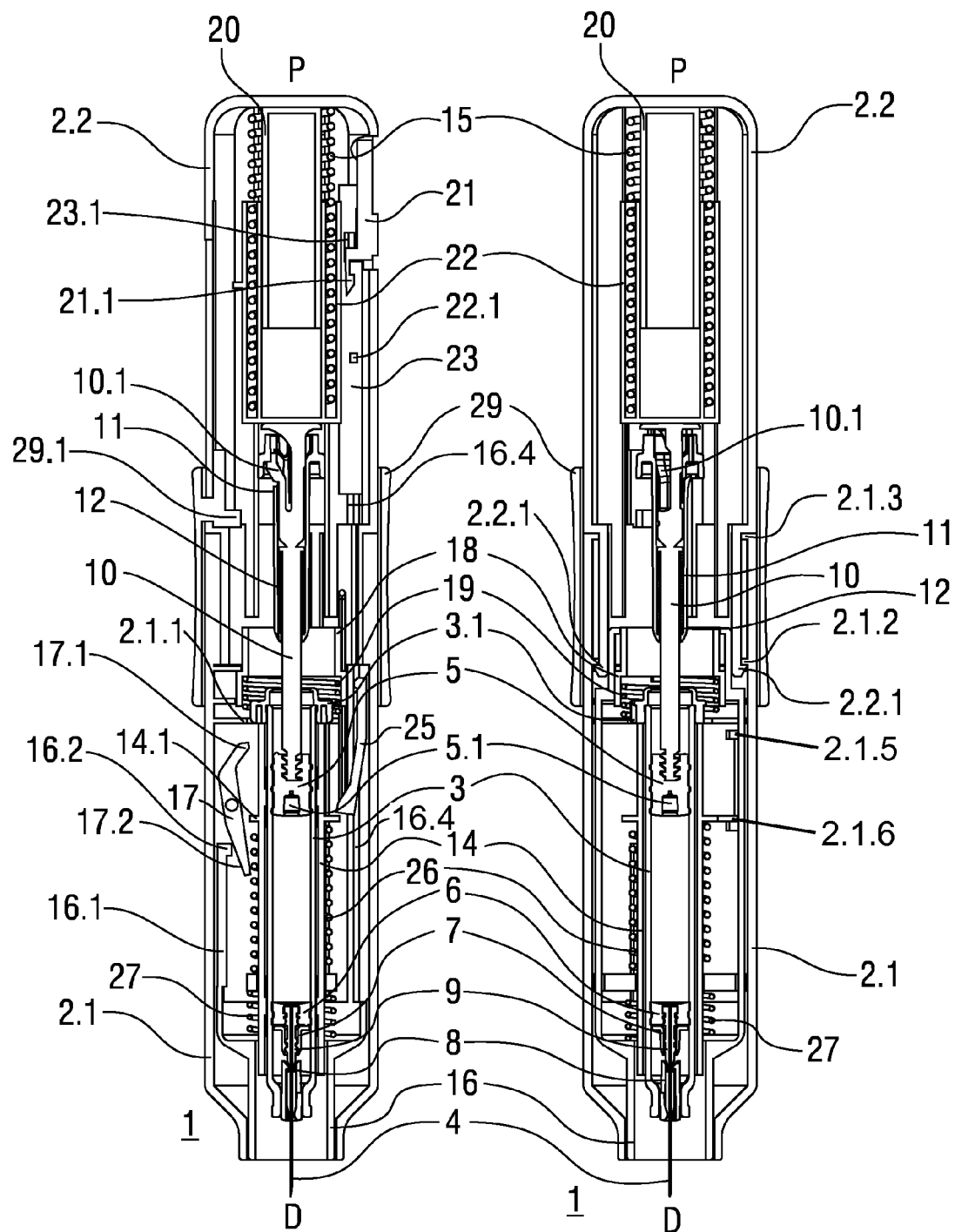
FIG. 6 shows an exemplary embodiment of an autoinjector with a needle extending from a distal end.

As shown in FIGS. 6A and 6B, when the trigger button 21 is pressed, the catch arm 21.1 on the trigger button 21 disengages the catch 22.1 and releases the drive carriage 22. The force from the expansion of the drive spring 15 pushes the drive carriage 22 in the distal direction D. Because the carrier 14 is not fixed relative to the front case 2.1, when the drive carriage 22 engages the inner plunger 10, the carrier 14 is displaced axially in the distal direction D relative to the front case 2.1 for needle insertion. Because friction opposing relative motion of the stopper 5 and the barrel is greater than the sum of the forces required to compress the carrier spring 26 and to insert the needle 4 into the injection site, the needle 4 is inserted without dispensing any medicament from the syringe 3.

As the carrier 14 moves axially in the distal direction D relative to the front case 2.1, the shoulder 14.1 on the carrier 14 engages, and temporarily deflects, the syringe forward latch 25. When the shoulder 14.1 bypasses the syringe forward latch 25, the syringe forward latch 25 returns to its non-deflected position, as shown in FIG. 6A.

The carrier 14 continues moving axially in the distal direction D relative to the front case 2.1 until the finger flange 3.1 on the syringe 3 abuts the third rib 2.1.1 in the front case 2.1. Needle penetration depth can be varied by varying an axial location of the third rib 2.1.1. Once the finger flange 3.1 abuts the third rib 2.1.1, the force on the stopper 5 is sufficient to overcome friction and emptying of the syringe 3 commences.

In another exemplary embodiment, axial movement of the carrier 14 is limited by a fifth rib 2.1.5 and a sixth rib 2.1.6. For example, a flange on the carrier 14 may abut the fifth rib 2.1.5 to limit retraction of the carrier 14 relative to the front case 2.1 and may abut the sixth rib 2.1.6 to limit distally directed movement of the carrier 14 relative to the front case 2.1 (which may, in part, define an injection depth).

Figures 7A, 7B:
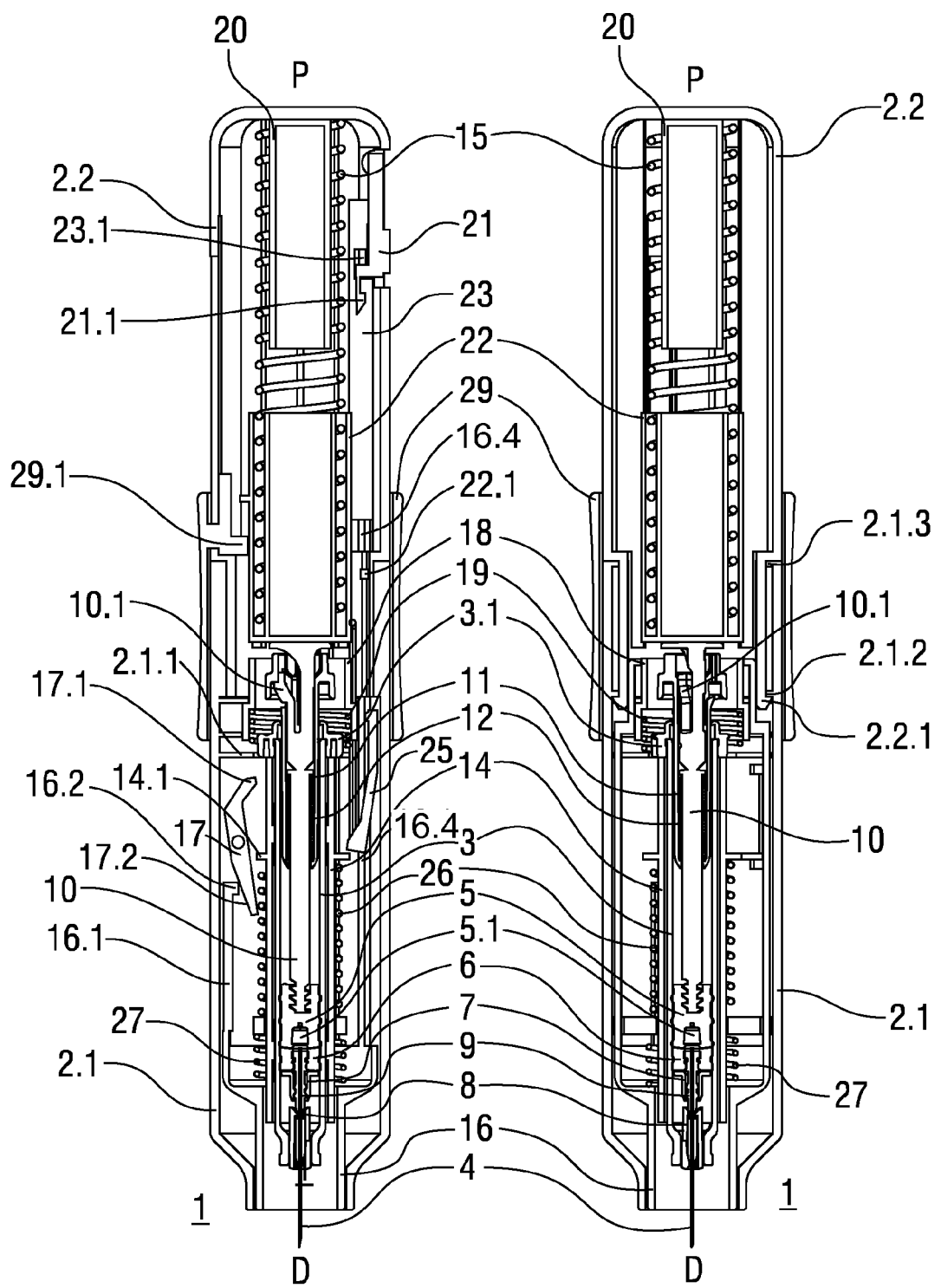
FIG. 7 shows an exemplary embodiment of an autoinjector near an end of dose.

FIGS. 7A and 7B show the autoinjector 1 when the syringe 3 is almost emptied. The stopper 5 has abutted the needle seal 6. As the stopper 5 advances further, it pushes the needle seal 6 and the ejector ring 7 in the distal direction D.

Figures 8A, 8B:
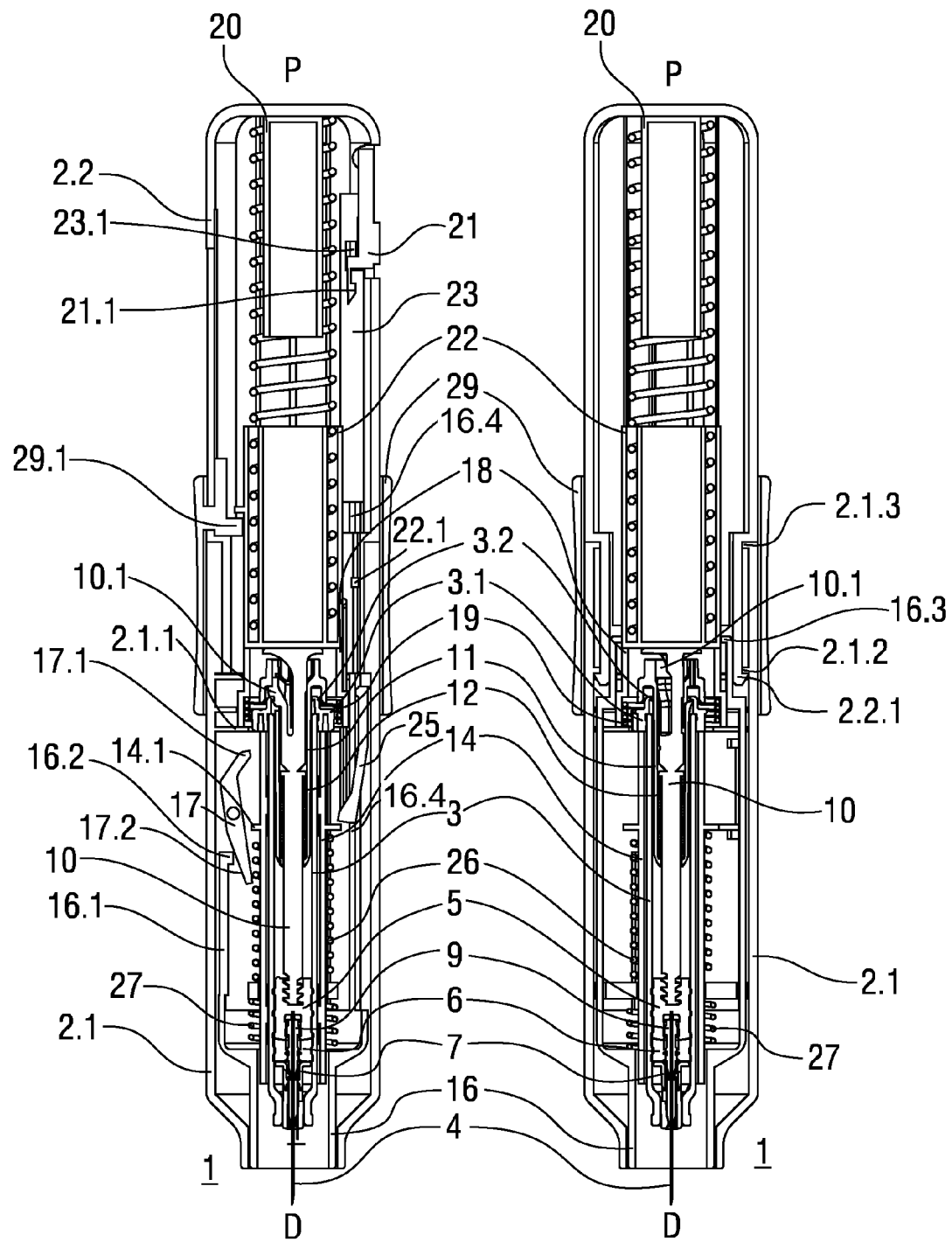
FIG. 8 shows an exemplary embodiment of an autoinjector at an end of dose.

As shown in FIGS. 8A and 8B, the drive carriage 21 abuts and pushes the latch sleeve 18 in the distal direction D against the biasing force of the latch sleeve spring 19 until the latch sleeve 18 abuts the third rib 2.1.1. At the same time, the inner plunger 10 pushes the stopper 5 and the needle seal 6 into abutment with the ejector ring 7 which abuts the needle retainer 8. When the ejector ring 7 engages the needle retainer 8, ramped distal arms on the ejector ring 7 deflect ramped proximal retainer arms on the needle retainer 8, releasing the needle mount 9 from the needle retainer 8. Substantially simultaneously, a proximal end of the needle mount 9 engages (e.g., frictionally, snap-fit, etc.) the cavity 5.1 in the stopper 5.

After the needle mount 9 has engaged the cavity 5.1, the release ring 3.2 causes the resilient arm 10.1 on the inner plunger 10 to deflect and release the outer plunger 11. The release ring 3.2 retains the outer plunger 11.

After delivering the dose, the drive carriage 22 abuts the latch sleeve 18.

When the autoinjector 1 is removed from the injection site, the interlock sleeve 16 translates in the distal direction D under the force of the sleeve spring 27 to ensure that the exposed needle 4 is covered, and the latch sleeve 18 is maintained abutting the third rib 2.1.1 by the force of the drive carriage 22. Thus, the proximal end of the interlock sleeve 16 no longer abuts the latch arms 2.2.1. Because the interlock sleeve 16 does not abut the latch arms 2.2.1, the force in the drive spring 15 causes the latch arms 2.2.1 to disengage the first rib 2.1.2. For example, the force in the drive spring 15 may be acting in the proximal direction P on the rear case 2.2 and in the distal direction D on the front case 2.1 (through the drive carriage 22 abutting the latch sleeve 18 which is compressed against the third rib 2.1.1). Due to this oppositely directed force, the latch arms 2.2.1 may deflect and disengage the first rib 2.1.2. When the latch arms 2.2.1 disengage the first rib 2.1.2, the drive carriage 22 may continue in the distal direction D until it abuts the shoulder 29.1 on the slider 29.

Figures 9A, 9B:
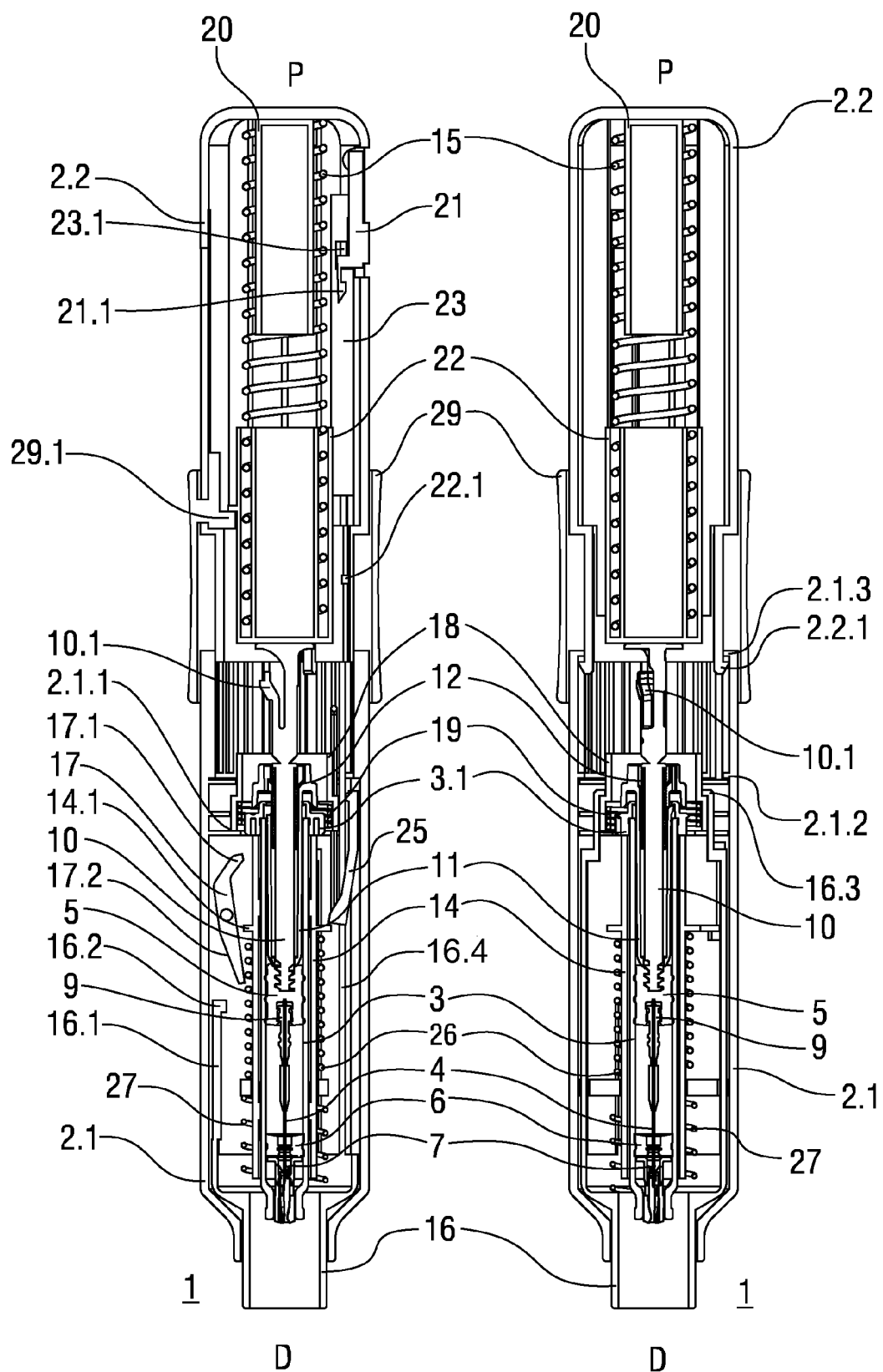
FIG. 9 shows an exemplary embodiment of an autoinjector after use.

As shown in FIGS. 9A and 9B, in an exemplary embodiment, the force of the plunger spring 12 pushes the inner plunger 11 (with the stopper 5 coupled to the needle mount 9) in the proximal direction P to withdraw the needle mount 9 and the needle 4 into the barrel of the syringe 3. When the inner plunger 11 abuts the drive carriage 22, the force of the plunger spring 12 is not strong enough to push the drive carriage 22 in the proximal direction P against the remaining force of the drive spring 15, so the front and rear cases 2.1, 2.2 move axially apart until the latch arms 2.2.1 engage the second rib 2.1.3. The force required for the latch arms 2.2.1 to disengage the first rib 2.1.2 may be varied by, for example, varying angles of corresponding ramped surfaces of latch arms 2.2.1 and the first rib 2.1.2.

Space created by relative displacement of the front case 2.1 and the rear case 2.2 and the syringe forward latch 25 abutting the shoulder 14.1 on the carrier 14, allows the inner plunger 11 (with the stopper 5 coupled to the needle mount 9) to move axially in the proximal direction P to withdraw the needle mount 9 and needle 4 into the barrel of the syringe 3.

Figures 10A, 10B:
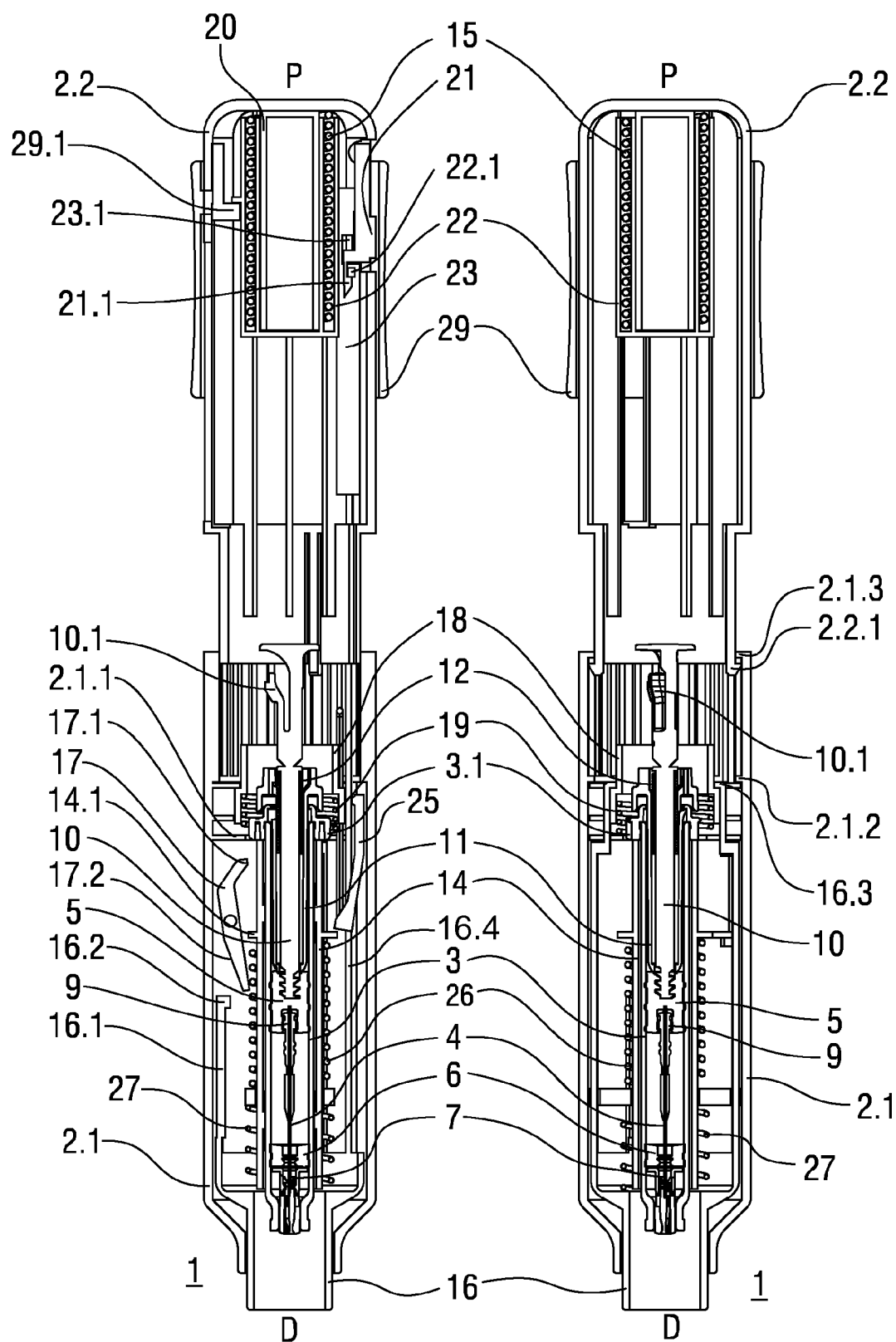
FIG. 10 shows an exemplary embodiment of an autoinjector when replacing a used syringe.

As shown in FIGS. 10A and 10B, the slider 29 is moved in the proximal direction P to reset the drive spring 15. The internal boss 29.1 on the resetting slider 29 engages the drive carriage 22 and slaves it in the proximal direction P as the slider 29 is translated thereby compressing the drive spring 15. As the drive carriage 22 moves in the proximal direction P, the catch 22.1 on the drive carriage 22 reengages the catch arm 21.1 on the trigger button 21.

Figures 11A, 11B:
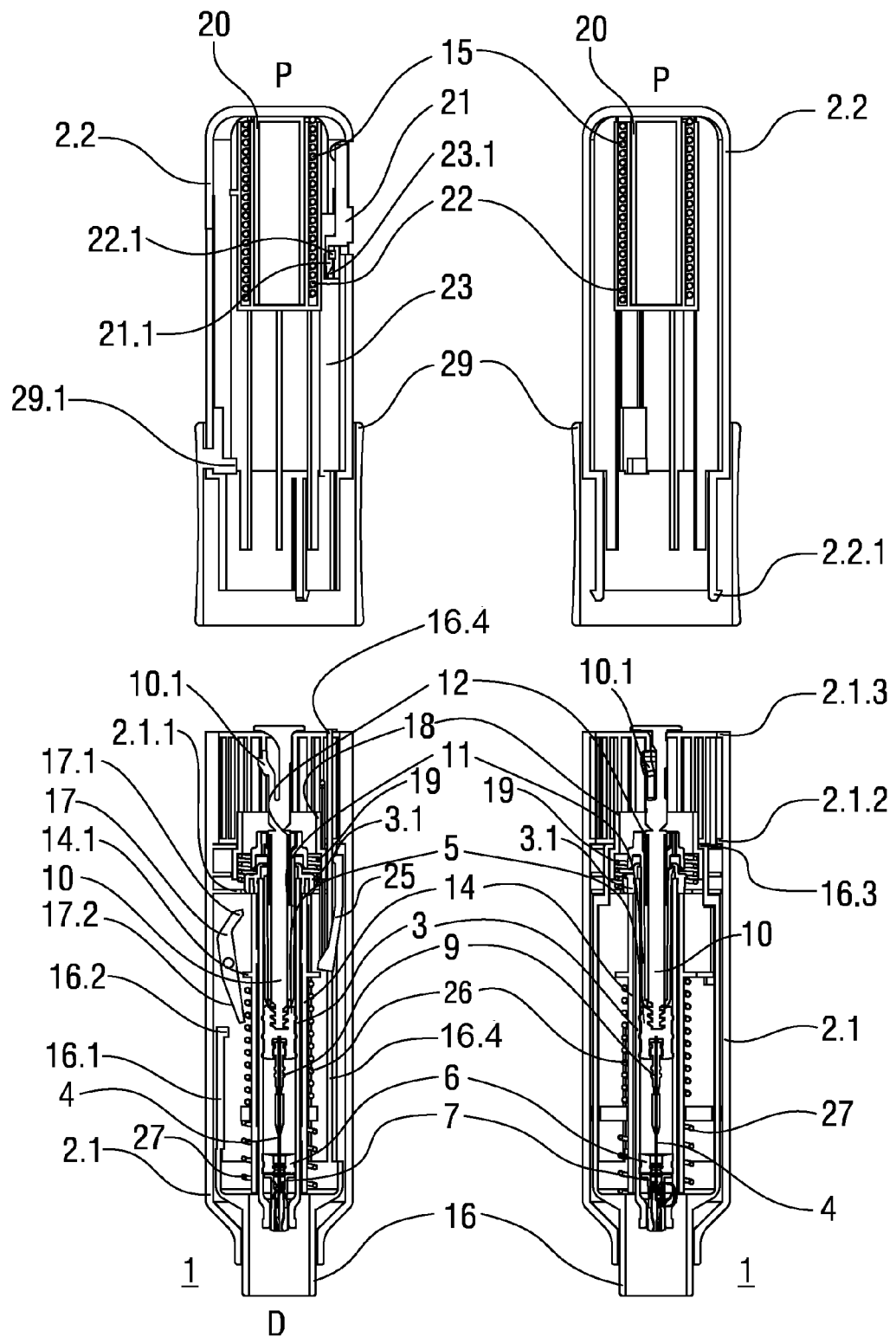
FIG. 11 shows an exemplary embodiment of an autoinjector when replacing a used syringe.

When the slider 29 has been fully retracted, the joint between the front case 2.1 and the rear case 2.2 is accessible, and the user can push the latch arms 2.2.1 radially inward to disengage them from the second rib 2.1.3 and separate the cases, as shown in FIG. 11A and 11B.

Figures 12A, 12B:
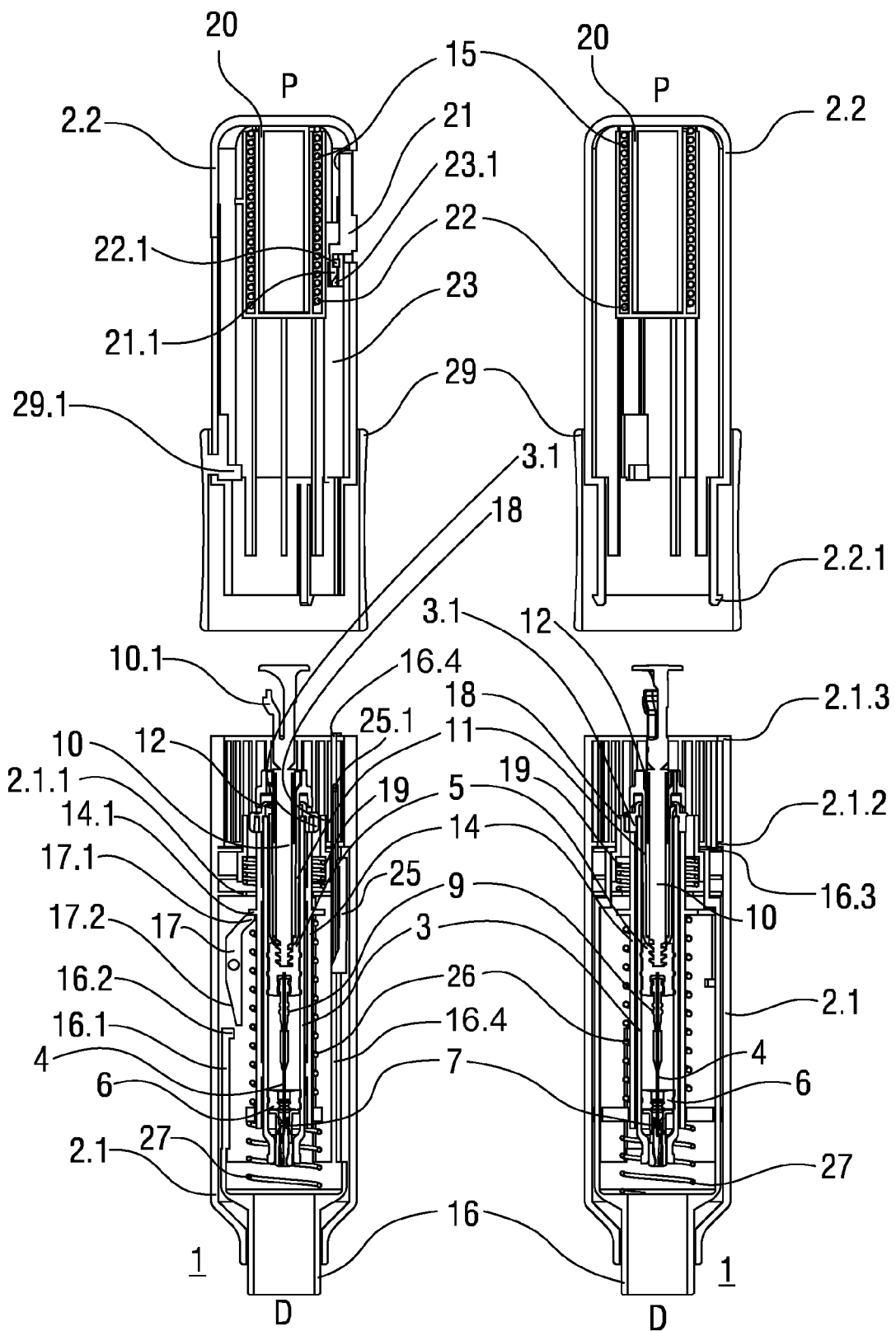
FIG. 12 shows an exemplary embodiment of an autoinjector when replacing a used syringe.

In FIGS. 12A and 12B, with the front and rear cases 2.1, 2.2 separated, the lever 25.1 connected to the syringe forwards latch 25 can be operated, e.g. by pushing the lever 25.1 in the distal direction D to deflect the syringe forwards latch 25 to disengage from the shoulder 14.1 on the carrier 14. The carrier spring 26, thus returns the carrier 14 and syringe 3 in the proximal direction P into their initial position. The user may now remove the syringe 3 from the carrier 14, and insert a new syringe.

As understood by those of skill in the art, while a syringe with a needle retraction mechanism has been described for use in the exemplary embodiments of the autoinjector 1, a syringe without any safety features (e.g., a Hypak syringe) may be used, and the autoinjector 1 may include one or more safety mechanisms, e.g., a locking mechanism for the interlock sleeve 16 to cover the needle 4.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
es Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
a front case having a first rib and a second rib, the front case being adapted to hold a syringe;
an interlock sleeve slidably disposed in the front case and adapted to project distally through a distal opening in the front case to contact an injection site;
a rear case telescopically coupled to the front case, the rear case having latch arms adapted to engage the first rib and the second rib, wherein, when the front case is in a first position relative to rear case, the latch arms are engaged to the first rib; and
a drive spring configured to (i) apply a force on the syringe to dispense a medicament from the syringe and (ii) cause the latch arms to disengage the first rib,
wherein, when the latch arms disengage the first rib, the front case translates to a second position relative to the rear case, an axial distance between the front case and the rear case increases relative to the first position, and the latch arms engage the second rib.

2. The autoinjector according to claim 1, further comprising:
a sleeve spring adapted to apply a biasing force to the interlock sleeve relative to the front case such that the interlock sleeve covers a needle of the syringe.

3. The autoinjector according to claim 1, further comprising:
a syringe carrier slidably disposed in the front case; and
a carrier spring adapted to apply a biasing force to the syringe carrier relative to the front case.

4. The autoinjector according to claim 3, further comprising:
a latch mechanism adapted to prevent movement of the syringe carrier in a distal direction relative to the front case.

5. The autoinjector according to claim 4, wherein the latch mechanism includes a syringe backward latch pivotable between a first angular position in which the syringe backward latch engages the syringe carrier and a second angular position in which the syringe backward latch disengages the syringe carrier.

6. The autoinjector according to claim 5, wherein the interlock sleeve includes an arm adapted to engage the syringe backward latch and move the syringe backward latch from the first angular position to the second angular position when the interlock sleeve moves relative to the front case.

7. The autoinjector according to claim 3, further comprising:
a latch mechanism adapted to prevent movement of the syringe carrier in a proximal direction relative to the front case.

8. The autoinjector according to claim 7, wherein the latch mechanism includes a resilient syringe forward latch adapted to deflect when the syringe carrier moves in a distal direction relative to the front case and return to a non-deflected position to abut the syringe carrier when the syringe carrier moves in the proximal direction relative to the front case.

9. The autoinjector according to claim 8, wherein the latch mechanism includes a lever coupled to the forward latch such that actuation of the lever causes the forward latch to disengage the syringe carrier.

10. The autoinjector according to claim 1, further comprising:
a latch sleeve slidably disposed in the front case; and
a latch sleeve spring adapted to apply a biasing force to the latch sleeve relative to the front case.

11. The autoinjector according to claim 10, wherein the latch sleeve prevents disengagement of the latch arms and the first rib until the latch sleeve is displaced against the biasing force of the latch sleeve spring.

12. The autoinjector according to claim 10, wherein the latch sleeve abuts the interlock sleeve in the first position to prevent the latch arms from disengaging the first rib.

13. The autoinjector according to claim 1, further comprising a drive carriage disposed in the rear case, wherein the drive spring is adapted to apply a force to the drive carriage relative to the rear case.

14. The autoinjector according to claim 13, further comprising:
a slider movably arranged on the rear case, wherein the slider includes an internal boss adapted to engage the drive carriage.

15. The autoinjector according to claim 1, further comprising: a trigger button disposed on the rear case.

16. The autoinjector according to claim 15, further comprising: a latch mechanism adapted to prevent actuation of the trigger button.

17. The autoinjector according to claim 16, wherein the latch mechanism includes a lockout bar slidably disposed in the rear case and having a recess, wherein the lockout bar abuts the trigger button to prevent movement of the trigger button until an arm on the interlock sleeve pushes the lockout bar in a proximal direction to align the recess with the trigger button.

18. The autoinjector according to claim 1, wherein the interlock sleeve abuts the latch arms in the first position to prevent the latch arms from disengaging the first rib.

19. The autoinjector according to claim 1, further comprising: a cap having resilient barbs adapted to engage a needle sheath.

20. The autoinjector according to claim 19, wherein the barbs are maintained in engagement with the needle sheath by the interlock sleeve.

21. The autoinjector according to claim 1, wherein the syringe has a needle retraction mechanism.

22. The autoinjector according to claim 21, wherein actuation of the needle retraction mechanism causes the front case to move from the first position to the second position.

23. The autoinjector according to claim 21, wherein when the needle retraction mechanism applies a force to a drive carriage disposed in the rear case, a remaining force in the drive spring prevents movement of the drive carriage relative to the rear case and causes axial movement of the front case relative to the rear case.

24. The autoinjector according to claim 1, wherein the front case and the rear case are configured to move axially apart such that an inner plunger of the syringe is movable proximally to withdraw a needle of the syringe into a barrel of the syringe.

\* \* \* \* \*